(12) United States Patent
Kiernan et al.

(10) Patent No.: US 11,642,165 B2
(45) Date of Patent: May 9, 2023

(54) CATHETER WITH MECHANICALLY EXPANDABLE ELEMENT HAVING FLEX CIRCUIT

(71) Applicant: BIOSENSE WEBSTER (ISRAEL) LTD., Yokneam (IL)

(72) Inventors: Patrick J. Kiernan, Pasadena, CA (US); Patrick O'Fallon, Laguna Hills, CA (US); Matthew W. Hitzeroth, Azusa, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1114 days.

(21) Appl. No.: 16/023,644

(22) Filed: Jun. 29, 2018

(65) Prior Publication Data

US 2020/0000518 A1    Jan. 2, 2020

(51) Int. Cl.
*A61B 18/14* (2006.01)
*A61B 17/00* (2006.01)
*A61B 18/00* (2006.01)

(52) U.S. Cl.
CPC .............. *A61B 18/1492* (2013.01); *A61B 2017/00243* (2013.01); *A61B 2018/00011* (2013.01); *A61B 2018/00214* (2013.01); *A61B 2018/00351* (2013.01)

(58) Field of Classification Search
CPC ...... A61B 18/1492; A61B 2018/00011; A61B 2018/00214; A61B 2018/00351; A61B 2017/00243
See application file for complete search history.

(56) References Cited

U.S. PATENT DOCUMENTS

| 5,345,936 A | 9/1994 | Pomeranz et al. |
| 5,738,096 A | 4/1998 | Ben-Haim |
| 8,357,152 B2 | 1/2013 | Govari et al. |

(Continued)

FOREIGN PATENT DOCUMENTS

| EP | 3 178 385 A1 | 6/2017 |
| EP | 3 332 727 A2 | 6/2018 |

OTHER PUBLICATIONS

International Search Report and Written Opinion dated Nov. 13, 2019 for Application No. PCT/IB2019/055362, 11 pgs.

*Primary Examiner* — Michael F Peffley
*Assistant Examiner* — Bo Ouyang
(74) *Attorney, Agent, or Firm* — Lewis Roca Rothgerber Christie LLP

(57) ABSTRACT

An apparatus includes a catheter and an end effector. At least a portion of the catheter is sized and configured to fit within a lumen of a human cardiovascular system. The end effector is positioned at a distal end of the catheter. The end effector includes an expandable assembly and at least one flex circuit. The expandable assembly is configured to transition between a non-expanded state and an expanded state. The expandable assembly includes at least one deformable strut or cage. Each flex circuit includes a flexible substrate secured, without an adhesive, to the expandable assembly and an electrode secured to the flexible substrate. The expandable assembly in the expanded state is configured to urge the electrode into contact with tissue. The electrode has a fishbone-like configuration that defines a longitudinally elongated portion and a plurality of fingers extending transversely from the longitudinally elongated portion.

20 Claims, 9 Drawing Sheets

(56) References Cited

U.S. PATENT DOCUMENTS

| | | |
|---|---|---|
| 8,956,353 B2 | 2/2015 | Govari et al. |
| 9,801,585 B2 | 10/2017 | Shah et al. |
| 9,907,480 B2 | 3/2018 | Basu et al. |
| 2002/0087208 A1* | 7/2002 | Koblish ............. A61B 18/1492 606/41 |
| 2005/0154386 A1* | 7/2005 | West .................. A61B 18/1492 606/41 |
| 2009/0240249 A1* | 9/2009 | Chan .................. A61B 18/1492 606/41 |
| 2011/0130648 A1 | 6/2011 | Beeckler et al. |
| 2012/0143298 A1* | 6/2012 | Just ........................ A61B 5/287 607/122 |
| 2013/0030426 A1 | 1/2013 | Gallardo et al. |
| 2015/0196354 A1* | 7/2015 | Haverkost .............. H05K 1/028 606/41 |
| 2017/0042614 A1* | 2/2017 | Salahieh ............ A61M 25/1011 |
| 2017/0042615 A1* | 2/2017 | Salahieh ............. A61B 5/6858 |
| 2017/0156840 A1 | 6/2017 | Edmiston et al. |
| 2017/0311829 A1* | 11/2017 | Beeckler .................... G03F 7/16 |
| 2017/0312022 A1 | 11/2017 | Beeckler et al. |
| 2018/0036078 A1 | 2/2018 | Ditter |
| 2018/0056038 A1 | 3/2018 | Aujla |
| 2018/0071017 A1 | 3/2018 | Bar-Tal et al. |

\* cited by examiner

CATHETER WITH MECHANICALLY EXPANDABLE ELEMENT HAVING FLEX CIRCUIT

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad that is in contact with the patient.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein; U.S. Pub. No. 2017/0312022, entitled "Irrigated Balloon Catheter with Flexible Circuit Electrode Assembly," published Nov. 2, 2017, the disclosure of which is incorporated by reference herein; U.S. Pub. No. 2018/0071017, entitled "Ablation Catheter with a Flexible Printed Circuit Board," published Mar. 15, 2018, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pub. No. 2018/0036078, entitled "Catheter with Soft Distal Tip for Mapping and Ablating Tubular Region," published Feb. 8, 2018, the disclosure of which is incorporated by reference herein; U.S. Pat. No. 8,956,353, entitled "Electrode Irrigation Using Micro-Jets," issued Feb. 17, 2015, the disclosure of which is incorporated by reference herein; and U.S. Pat. No. 9,801,585, entitled "Electrocardiogram Noise Reduction," issued Oct. 31, 2017, the disclosure of which is incorporated by reference herein.

Some catheter ablation procedures may be performed using electrophysiology (EP) mapping. Such EP mapping may include the use of sensing electrodes on a catheter (e.g., the same catheter that is used to perform the ablation). Such sensing electrodes may monitor electrical signals within the cardiovascular system to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of an EP mapping catheter is described in U.S. Pat. No. 9,907,480, entitled "Catheter Spine Assembly with Closely-Spaced Bipole Microelectrodes," issued Mar. 6, 2018, the disclosure of which is incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif.

While several ablation catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Ablation System

Figure 1:
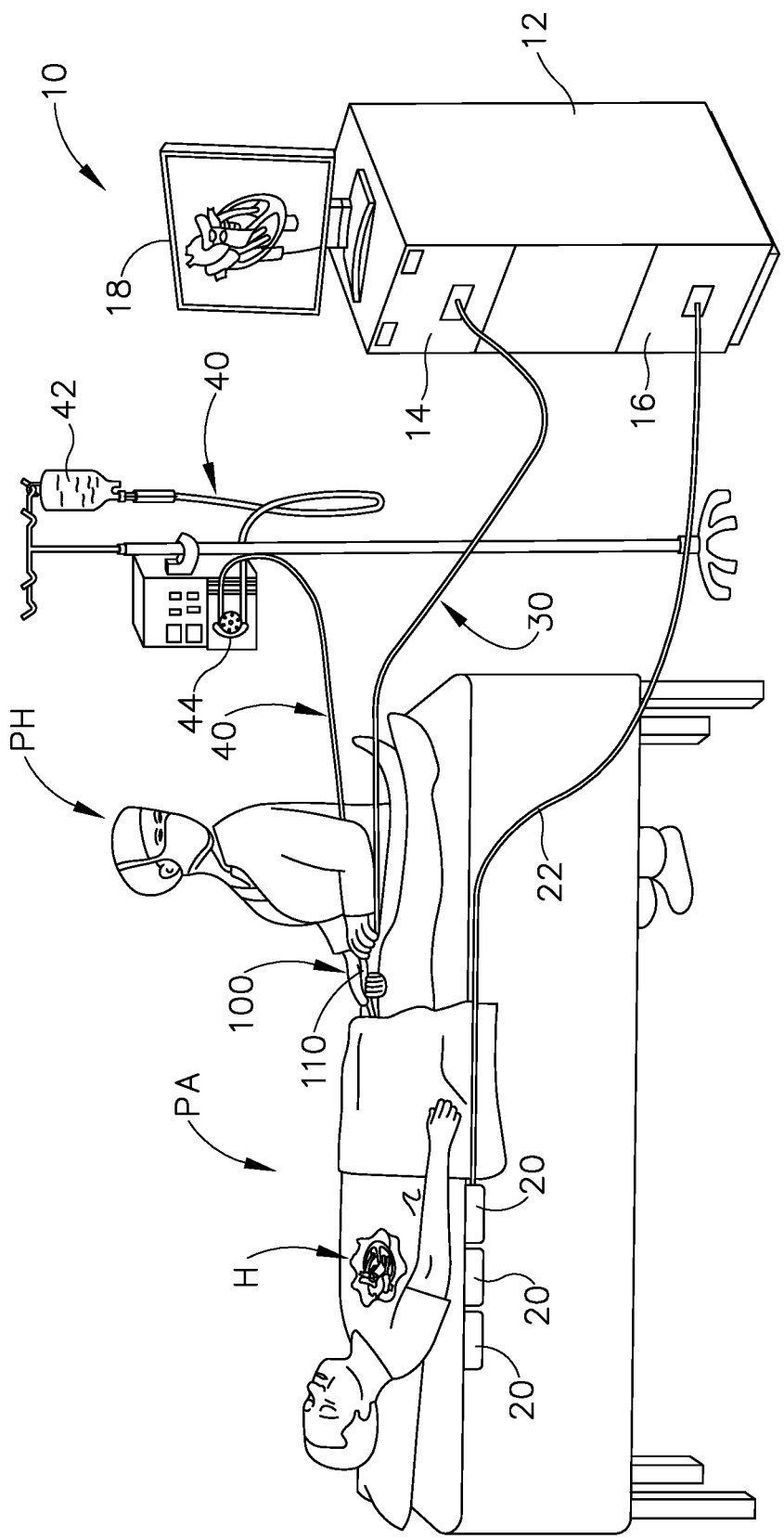
FIG. 1 depicts a schematic view of a medical procedure in which an ablation catheter of an ablation catheter assembly is inserted in a patient.

FIG. 1 shows an exemplary medical procedure and associated components of a cardiac ablation system. In particular, FIG. 1 shows a physician (PH) grasping a handle (110) of an ablation catheter assembly (100), with an end effector (200) of an ablation catheter (120) (shown in FIGS. 2A-2B but not shown in FIG. 1) of ablation catheter assembly (100) disposed in a patient (PA) to ablate tissue in or near the heart (H) of the patient (PA). Ablation catheter assembly (100) is coupled with a guidance and drive system (10) via a cable (30). Ablation catheter assembly (100) is also coupled with a fluid source (42) via a fluid conduit (40), though this is merely optional. A set of field generators (20) are positioned underneath the patient (PA) and are also coupled with guidance and drive system (10) via a cable (22).

Guidance and drive system (10) of the present example includes a console (12) and a display (18). Console (12) includes a first driver module (14) and a second driver module (16). First driver module (14) is coupled with ablation catheter assembly (100) via cable (30) and is operable to provide RF power to electrodes (250) of end effector (200) as will be described in greater detail below. In some versions, first driver module (14) is also operable to receive EP mapping signals from electrodes (174 or 250). Console (12) includes a processor (not shown) that processes such EP mapping signals and thereby provides EP mapping as is known in the art. In some versions, first driver module (14) is also operable to receive position indicative signals from a position sensor (not shown) in end effector (200), as will be described in greater detail below. In such versions, the processor of console (12) is also operable to process the position indicative signals from the position sensor to thereby determine the position of the end effector (200) of ablation catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Figure 3:
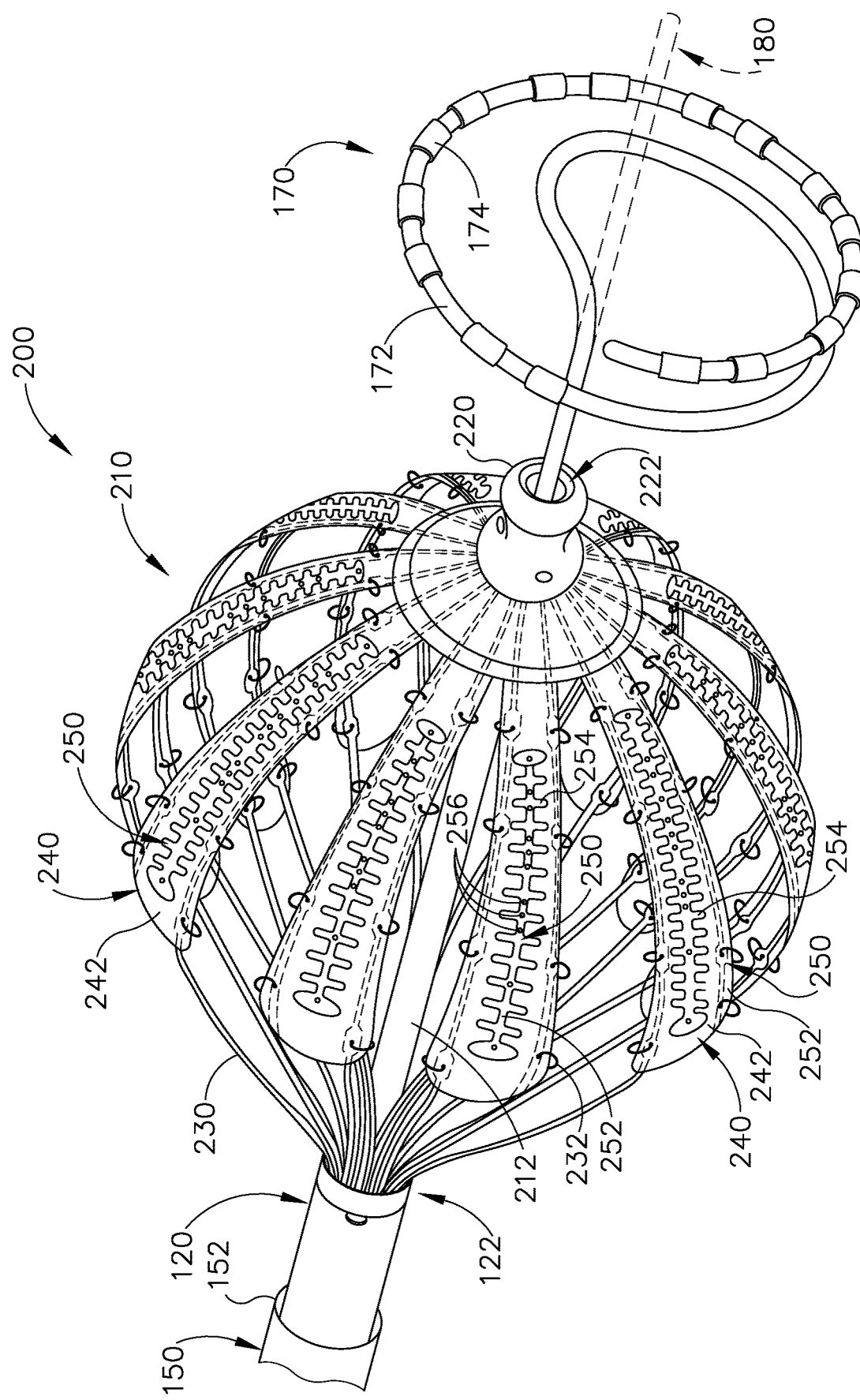
FIG. 3 depicts a perspective view of the end effector of FIG. 2A, with the expandable assembly in the expanded state.

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the position sensor of end effector (200). For instance, as end effector (200) of ablation catheter (120) moves within the patient (PA), the corresponding position data from the position sensor may cause the processor of console (12) to update the patient anatomy views in display (18) in real time to depict the regions of patient anatomy around end effector (200) as end effector (200) moves within the patient (PA). Moreover, the processor of console (12) may drive display (18) to show locations of aberrant conductive tissue sites, as detected via EP mapping with end effector (200) or as detected via EP mapping with a dedicated mapping catheter (170) (FIG. 3). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (200) on the images of the patient's anatomy, such as by superimposing an illuminated dot, a crosshair, a graphical representation of end effector (200), or some other form of visual indication. Such a superimposed visual indication may also move within the images of the patient anatomy on display (18) in real time as the physician moves end effector (200) within the patient (PA), thereby providing real-time visual feedback to the operator about the position of end effector (200) within the patient (PA) as end effector (200) moves within the patient (PA). The images provided through display (18) may thus effectively provide a video tracking the position of end effector (200) within a patient (PA), without necessarily having any optical instrumentation (i.e., cameras) viewing end effector (200). In the same view, display (18) may simultaneously visually indicate the locations of aberrant conductive tissue sites detected through the EP mapping as described herein. The physician (PH) may thus view display (18) to observe the real time positioning of end effector (200) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44). Pump (44) is positioned along conduit (40) between fluid source (42) and ablation catheter assembly (100). In the present example, pump (44) includes a peristaltic pump that is operable to selectively drive fluid from fluid source (42) to ablation catheter assembly (100). Alternatively, pump (44) may take any other suitable form.

In some variations, conduit (40), fluid source (42), and pump (44) are omitted entirely. In versions where these components are included, end effector (200) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

Figure 2A:
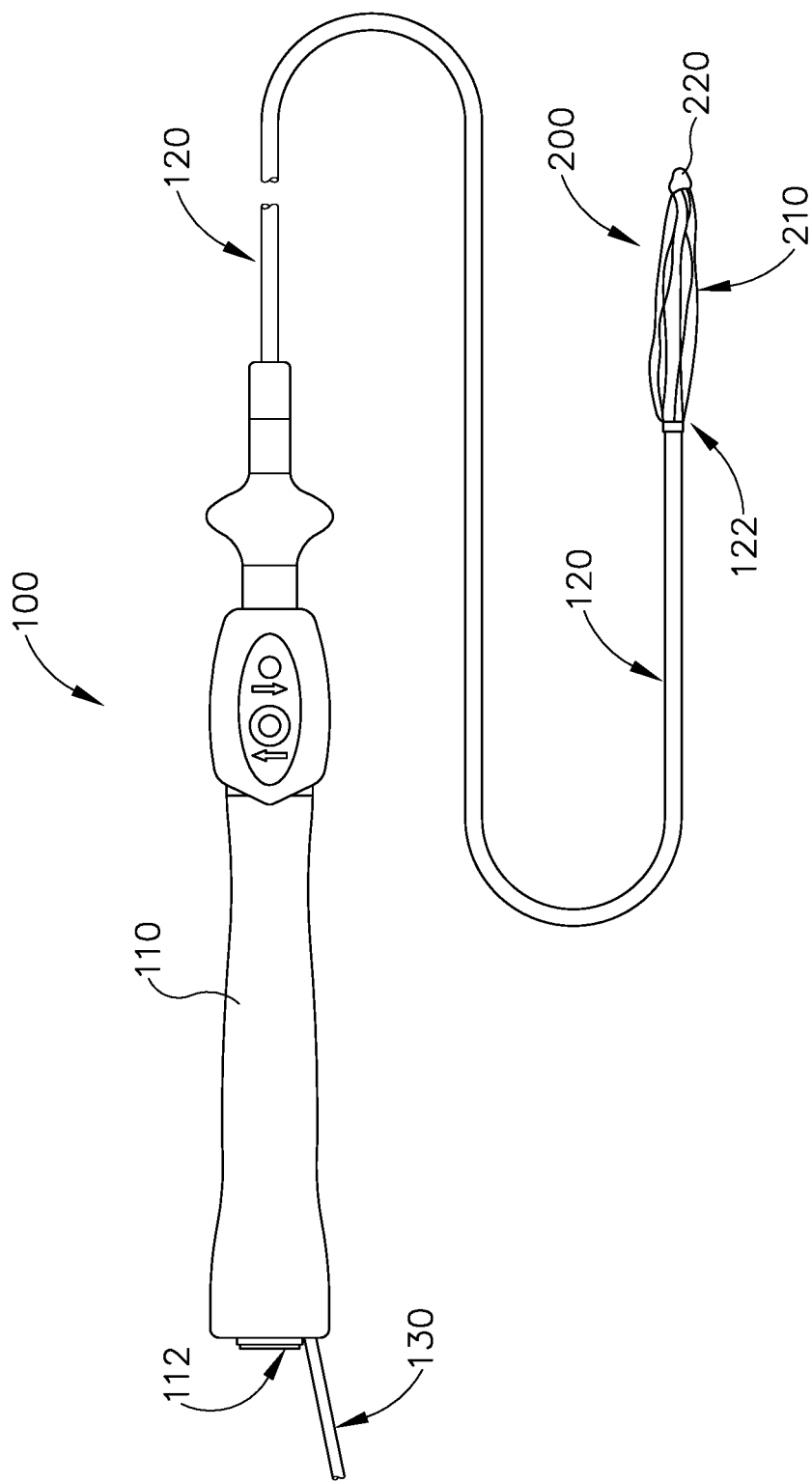
FIG. 2A depicts a top plan view of the ablation catheter assembly of FIG. 1, with an expandable assembly of an end effector in a non-expanded state.
Figure 2B:
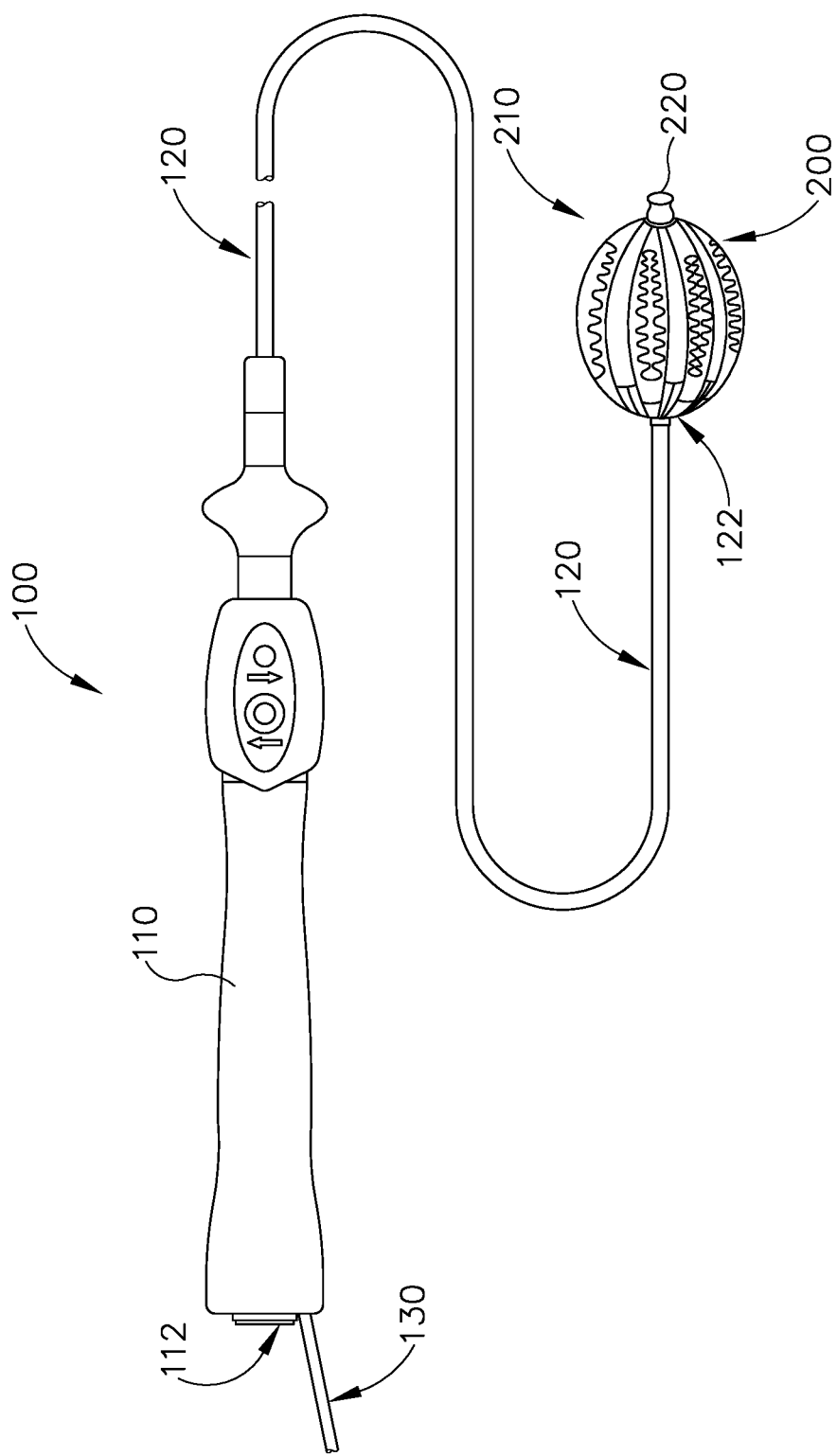
FIG. 2B depicts a top plan view of the ablation catheter assembly of FIG. 1, with the expandable assembly of the end effector in an expanded state.

FIGS. 2A-2B show ablation catheter assembly (100) in greater detail. As shown, ablation catheter (120) extends distally from handle (110); while a fluid connector assembly (130) extends proximally from handle (110). Fluid connector assembly (130) is configured to couple with conduit (40) to thereby provide a path for irrigation fluid to be communicated from fluid source (42) to end effector (200). As fluid irrigation is a merely optional feature of ablation catheter assembly (100), fluid connector assembly (130) may be omitted if desired. Handle (110) of the present example also includes a socket (112), which is configured to receive a plug (not shown) on the distal end of cable (30) to thereby provide a path for electrical communication between console (12) and end effector (200). Various suitable components and configurations that may be used to form these components will be apparent to those skilled in the art in view of the teachings herein.

II. Exemplary End Effector with Expandable Assembly having Flex Circuits

As also shown in FIGS. 2A-2B, end effector (200) is positioned at the distal end (122) of ablation catheter (120). End effector (200) is configured to transition between a non-expanded configuration (FIG. 2A) and an expanded configuration (FIG. 2B). End effector (200) may be kept in the non-expanded configuration as ablation catheter (120) is inserted into the patient (PA). Once end effector (200) reaches a target site in the patient, end effector (200) may be transitioned to the expanded configuration. Some examples of how end effector (200) may be transitioned between the non-expanded configuration and the expanded configuration will be described in greater detail below, while other examples will be apparent to those skilled in the art in view of the teachings herein.

FIG. 3 shows end effector (200) in greater detail, in the expanded configuration. End effector (200) is positioned distally of the distal end (152) of an outer sheath (150). In some scenarios, ablation catheter (120) is slidably disposed in outer sheath (150); and ablation catheter (120) and outer sheath (150) are advanced together into lumen (e.g., artery, vein, etc.) of the patient (PA) until distal end (152) is near a target site in the patient (PA). End effector (200) may be initially retracted proximally relative to distal end (152) as the combination of ablation catheter (120) and outer sheath (150) are advanced into position. Once reaching the target site, ablation catheter (120) may be advanced distally as outer sheath (150) is held stationary, to thereby advance end effector (200) from distal end (152). Alternatively, ablation catheter (120) may be held stationary as outer sheath (150) is retracted proximally to reveal end effector (200). In still other versions, outer sheath (150) is omitted.

End effector (200) of this example includes an expandable assembly (210), a central shaft (212), and a distal hub (220). Expandable assembly (210) includes a set of struts (230), which are wires or beams that form a frame supporting a set of flex circuit assemblies (240). Struts (230) extend longitudinally from the distal end (122) of ablation catheter (120), generally converging at distal hub (220). By way of example only, the proximal ends of struts (230) may be joined with distal end (122) of ablation catheter (120) via an interlocking joint, which may be formed of a polymer or any other suitable material(s). In some variations, one or more additional wires, beams, or other structural members extend transversely between adjacent struts (230). By way of example only, struts (230) may be formed of nitinol, self-expanding polymers, or any other suitable material(s). Struts (230) are angularly spaced apart from each other and are configured to bow outwardly to provide end effector (200) with a generally bulbous configuration when expandable assembly (210) is in the expanded configuration. In some versions, struts (230) are resiliently biased to assume the outwardly bowed configuration. In some such versions, outer sheath (150) constrains struts (230) when outer sheath (150) is positioned over end effector (200), thereby maintaining expandable assembly (210) in the non-expanded configuration until end effector (200) is positioned distally in relation to distal end (152) of outer sheath (150).

As another merely illustrative example, expandable assembly (210) may be selectively driven by an actuator to transition expandable assembly (210) between the expanded and non-expanded configurations. For instance, in some such versions, central shaft (212) is longitudinally fixed to distal hub (220) and relative to handle (110). A translating actuation assembly (e.g., push rod, push wire, etc.) (not shown) is coupled with the proximal ends of struts (230). When the actuation assembly is advanced from a proximal position to a distal position, the proximal ends of struts (230) translate distally while the distal ends of struts (230) remain longitudinally stationary, thereby causing struts (230) to buckle and bow outwardly, thereby transitioning expandable assembly (210) to the expanded state. When the actuation assembly is retracted from the distal position to the proximal position, the proximal ends of struts (230) translate proximally while the distal ends of struts (230) remain longitudinally stationary, thereby causing struts (230) to generally straighten, thereby transitioning expandable assembly (210) to the non-expanded state.

As another variation, the proximal ends of struts (230) may be longitudinally fixed relative to handle (110), and the actuation assembly may be coupled with distal hub (220). When the actuation assembly (e.g., pull wire, etc.) is retracted from a distal position to a proximal position, the distal ends of struts (230) translate proximally while the proximal ends of struts (230) remain longitudinally stationary, thereby causing struts (230) to buckle and bow outwardly, thereby transitioning expandable assembly (210) to the expanded state. When the actuation assembly is advanced from the proximal position to the distal position, the distal ends of struts (230) translate distally while the proximal ends of struts (230) remain longitudinally stationary, thereby causing struts (230) to generally straighten, thereby transitioning expandable assembly (210) to the non-expanded state. Other suitable ways in which expandable assembly may transition between the non-expanded state and the expanded state will be apparent to those skilled in the art in view of the teachings herein. It should also be understood that struts (230) may have various other suitable configurations and associated components. Moreover, expandable assembly (210) may have various other components and configurations, some examples of which will be described in greater detail below.

Figure 4:
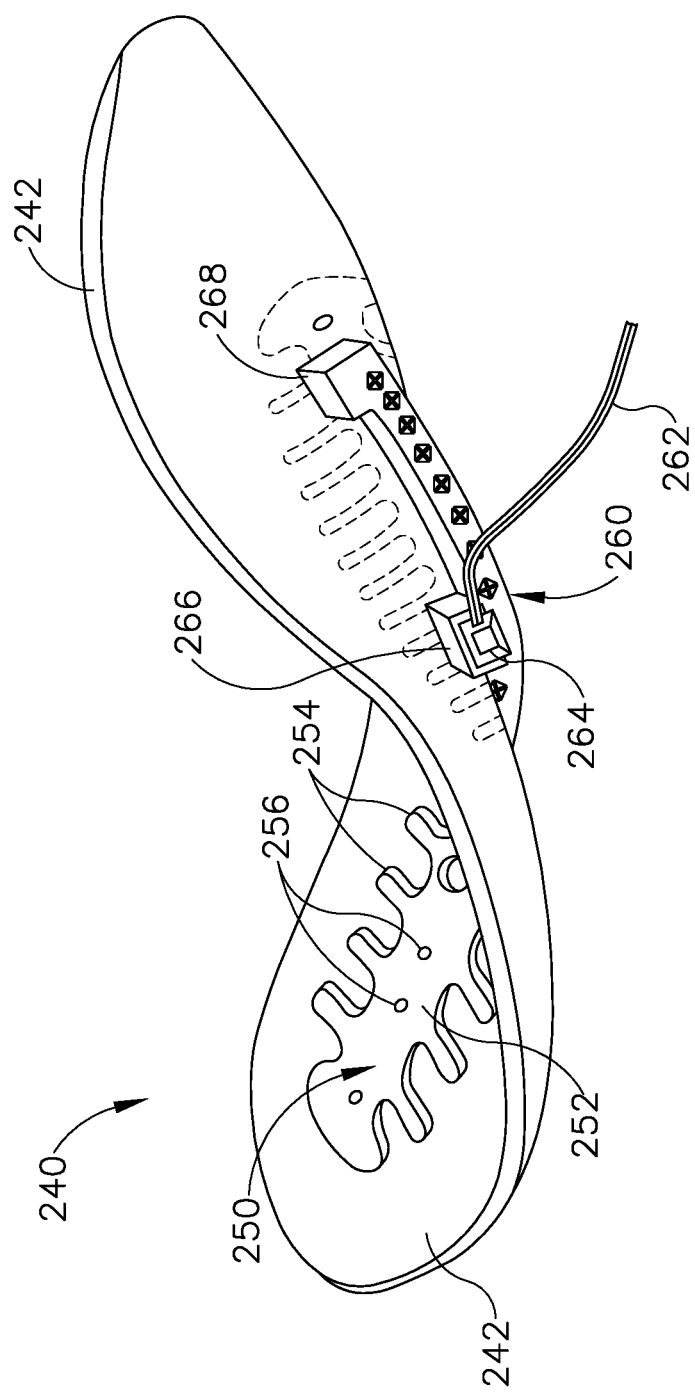
FIG. 4 depicts a perspective view of a flex circuit of the end effector of FIG. 2A, with a portion of the flex circuit bent over to reveal an underside.

Each flex circuit assembly (240) is secured to a respective pair of struts (230) in the present example. FIG. 4 shows a flex circuit assembly (240) in greater detail. As shown, flex circuit assembly (240) includes a flexible substrate (242) and an electrode (250) adhered to flexible substrate (242). Electrode (250) includes a central elongated portion (252) or spine, with a plurality of fingers (254) extending transversely from elongated portion (252). Electrode (250) thus has a fishbone configuration. With such a fishbone configuration, fingers (254) may advantageously increase the circumferential or equatorial contact surface of electrode (250) with the targeted tissue, while the gaps between adjacent fingers (254) may advantageously allow expandable assembly (210) to collapse inwardly and/or expand radially as needed at locations along its equator. In some versions, fingers (254) have different lengths, with some being longer and others being shorter. For instance, fingers (254) may have progressively decreasing lengths along the length of elongated portion (252), providing electrode (250) with a generally tapered configuration. Electrodes (250) may be further constructed and operable in accordance with at least some of the teachings of U.S. Pub. No. 2017/0312022, entitled "Irrigated Balloon Catheter with Flexible Circuit Electrode Assembly," published Nov. 2, 2017, the disclosure of which is incorporated by reference herein.

A longitudinally extending array of blind vias (256) are positioned along elongated portion (252). Blind vias (256) are electrically conductive formations that pass through electrode (250) and flexible substrate (242) to electrically couple electrode (250) with a wired assembly (260) on the underside of flexible substrate (242). Wired assembly (260) includes a wire (262) that extends to a weld (264) on a pad (266). Pad (266) is secured to a longitudinally extending electrode (268), with is further coupled with blind vias (256). By way of example only, electrode (268) may be secured to the underside of flexible substrate (242) via sewing or using any other suitable components or techniques. Weld (264), pad (266), electrode (268), and blind vias (256) thus cooperate to provide a path for electrical communication between electrode (250) and wire (262). Wire (262) is further coupled with cable (30), thereby coupling electrode (250) with console (12). Other suitable ways in which electrodes (250) may be coupled with console (12) will be apparent to those skilled in the art in view of the teachings herein.

Figure 5:
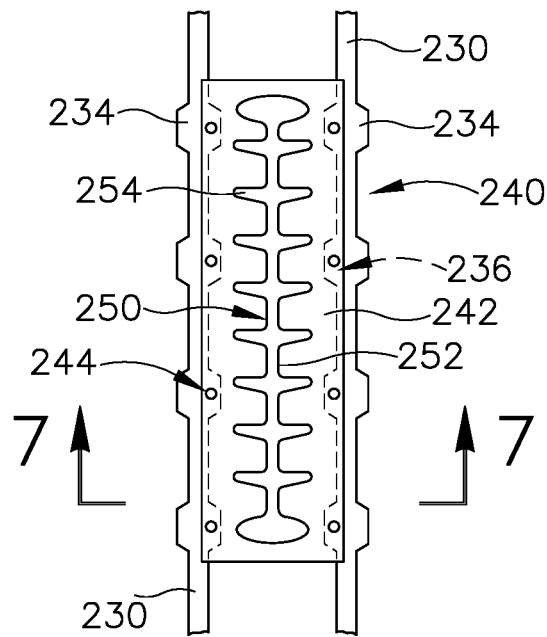
FIG. 5 depicts a top plan view of a portion of the end effector of FIG. 2A, according to one example of features to secure the flex circuit of FIG. 4 to struts of the expandable assembly.

As shown in FIG. 3, flex circuit assemblies (240) are secured to respective pairs of struts (230) via suture loops (232). FIG. 5 shows exemplary features that may be provided to accommodate such suture loops (232). As shown, each strut (230) is in the form of an elongate strip of material, with coupling tabs (234) formed at discrete positions along the length of the elongate strip of material. Each coupling tab (234) defines an opening (236). Flexible substrate (242) also defines a set of openings (244). Openings (244) are positioned such that each opening (244) along one lateral side of flexible substrate (242) will align with openings (236) along the strut (230) that is positioned along that lateral side of flexible substrate (242); while each opening (244) along the other lateral side of flexible substrate (242) will align with openings (236) along the strut (230) that is positioned along the other lateral side of flexible substrate (242). With corresponding openings (236, 244) aligned, a suture loop (232) may be passed through each pair of openings (236, 244) to thereby secure flex circuit assembly (240) to the pair of struts (230). By way of example only, suture loops (232) may be formed of a high tensile polymer fiber, polyester (e.g., Dacron), polypropylene, stainless steel, or any other suitable material(s). Each suture loop (232) may also be in the form of a monofilament or any other suitable form.

Figure 6:
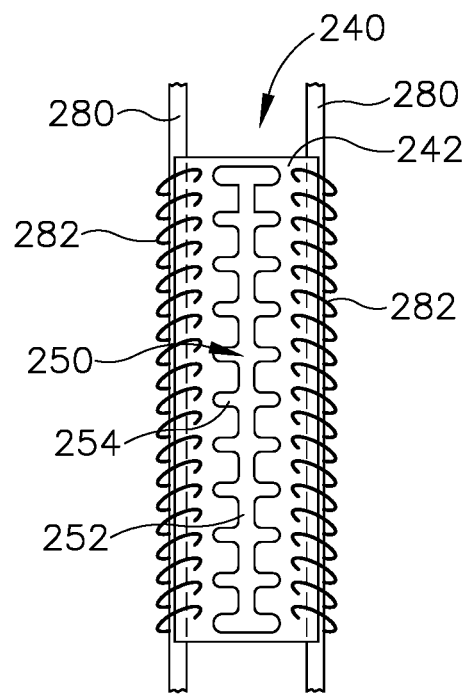
FIG. 6 depicts a top plan view of a portion of the end effector of FIG. 2A, according to another example of features to secure the flex circuit of FIG. 4 to struts of the expandable assembly.

FIG. 6 shows another merely illustrative way in which a flex circuit assembly (240) may be secured to a pair of struts (280). Struts (280) of this example are identical to struts (280) described above, except that struts (280) of this example lack coupling tabs (234). Flex circuit assembly (240) of this example is secured to struts (280) via sutures (282). In this example, a first suture (282) is stitched helically along one lateral side of flexible substrate (242), capturing the strut (280) underlying that lateral side of flexible substrate (242); and a second suture (282) is stitched helically along the other lateral side of flexible substrate (242), capturing the strut (280) underlying that other lateral side of flexible substrate (242). Again, suture (282) may be formed of high tensile polymer fiber, polyester (e.g., Dacron), polypropylene, stainless steel, or any other suitable material(s). Each suture (282) may also be in the form of a monofilament or any other suitable form. One merely illustrative variation of the example shown in FIG. 6 may include one or more features like coupling tabs (234) on each strut (280), thereby promoting longitudinal fixation of at least one end of flexible substrate (242) along struts (280).

Figure 7:
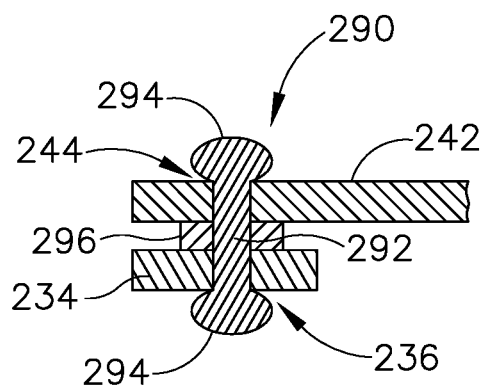
FIG. 7 depicts a cross-section of a lateral portion of the portion of the end effector of FIG. 5, taken along line 7-7 of FIG. 5, including a rivet securing the flex circuit of FIG. 4 to a strut of the expandable assembly.
Figure 8:
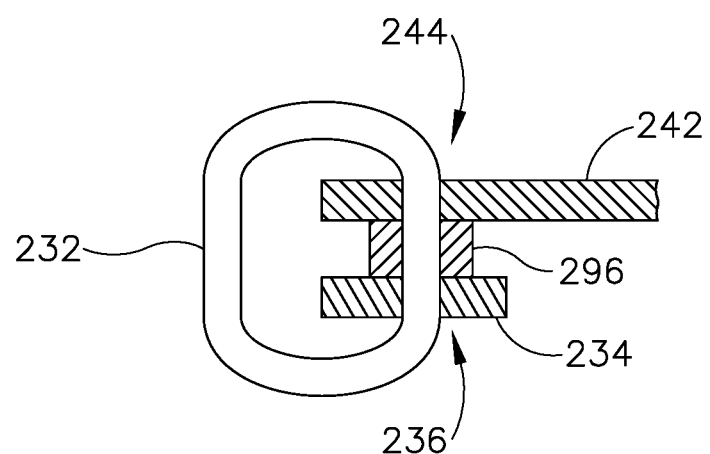
FIG. 8 depicts a cross-section of a lateral portion of the portion of the end effector of FIG. 5, taken along line 7-7 of FIG. 5, including a suture loop securing the flex circuit of FIG. 4 to a strut of the expandable assembly.

FIG. 7 shows another merely illustrative way in which flex circuit assembly (240) may be secured to strut (280). In this example, a rivet (290) is used in place of suture loop (232). Rivet (290) of this example has a central shaft (292) with a head (294) at each end of shaft (292). Each head (294) has an outer diameter that is larger than the diameter of each opening (236, 244). Shaft (292) passes through openings (236, 244), with one head (294) bearing against flexible substrate (242) and the other head (294) bearing against coupling tab (234). By way of example only, rivet (290) may be formed of a polymer monofilament or any other suitable material(s). As another merely illustrative example, rivet (290) may be formed of a metallic material coated with an electrically insulative material. As also shown in FIG. 7, an insulating layer (296) is interposed between flexible substrate (242) and coupling tab (234), thereby providing electrical isolation between flex circuit assembly (240) and strut (280). FIG. 8 shows the same kind of insulating layer (296) being used in an example that incorporates suture loop (232) as described above. An insulating layer (296) may also be used in versions where suture (282) is used as described above with reference to FIG. 6.

During use of ablation catheter assembly (100), ablation catheter (120) may be advanced to position end effector (200) near a targeted cardiovascular structure adjacent to the heart (e.g., the pulmonary vein) while end effector (200) is in the non-expanded configuration. End effector (200) may then be expanded to bring electrodes (250) into contact with the tissue of the targeted cardiovascular structure. In some versions, the operator may selectively actuate expandable assembly (210) to provide a desired degree of expansion, with the degree of expansion being selected based on the dimensions or structural configuration of the particular anatomical structure that is being targeted. For instance, in versions where an actuator such as a pull wire is used to transition expandable assembly (210) from the non-expanded configuration to the expanded configuration, the operator may translate the actuator to a distance selected to achieve a degree of expansion that will result in expandable assembly (210) just bringing electrodes (250) into contact with the tissue of the anatomical structure. This may enable the operator to avoid over-expanding expandable assembly (210) and thereby potentially causing damage to the anatomical structure.

After expandable assembly (210) appropriately urges electrodes (250) into contact with the target tissue, electrodes (250) may then be activated to apply RF energy to the tissue, to thereby ablate the tissue. The RF energy may be supplied from console (12) via the various components electrically coupling electrodes (250) with console (12) as described above. End effector (200) may then be collapsed to the non-expanded configuration. End effector (200) may then be repositioned to another location, with above-described steps being repeated, to ablate tissue at the other location. After the ablation is complete, ablation catheter (120) may be removed from the patient (PA).

As noted above, some versions of use may include the communication of irrigation fluid from fluid source (42) to the targeted tissue site while the ablation is being performed. Such irrigation may provide cooling to prevent undue thermal damage to the tissue. As an alternative to providing irrigation, the patient's own blood may provide a cooling effect, such that irrigation fluid from fluid source (42) is not needed. In other words, the expanded end effector (200) provides substantial gaps between regions of struts (230) that are not covered by flex circuit assemblies (240). The patient's blood may flow freely through such gaps, thereby providing an irrigation effect. To further promote the flow of blood through the expanded end effector (200), flexible substrate (242) may include a plurality of openings formed therethrough.

Referring back to FIG. 3, distal hub (220) of the present example also defines an opening (222) that is sized to allow other instruments to pass through end effector (200). For instance, FIG. 3 shows a lasso catheter (170) protruding through opening (222) and positioned distally of end effector (200). Lasso catheter (170) includes a helical body portion (172) with a plurality of electrodes (174) spaced therealong. By way of example only, lasso catheter (170) may be configured and operable in accordance with at least some of the teachings of U.S. Pub. No. 2018/0036078, entitled "Catheter with Soft Distal Tip for Mapping and Ablating Tubular Region," published Feb. 8, 2018, the disclosure of which is incorporated by reference herein. FIG. 3 also shows another catheter (180) (in broken lines) protruding through opening (222) and positioned distally of end effector (200). Catheter (180) may include a force sensor or any other suitable feature(s). By way of example only, catheter (180) may be configured and operable in accordance with at least some of the teachings of U.S. Pat. No. 8,357,152, entitled "Catheter with Pressure Sensing," issued Jan. 22, 2013, the disclosure of which is incorporated by reference herein; U.S. Pub. No. 2011/0130648, entitled "Catheter with Pressure Measuring Tip," published Nov. 30, 2009; or any other patent reference cited herein. Other suitable instruments that may be passed through opening (222) will be apparent to those skilled in the art in view of the teachings herein.

In some variations, end effector (200) includes a position sensor (not shown) that is operable to generate signals that are indicative of the position and orientation of end effector (200) within the patient (PA). By way of further example only, such a position sensor may be incorporated into another instrument that is associated with end effector (200), such as lasso catheter (170) or catheter (180). In some versions, the position sensor includes a wire coil or a plurality of wire coils (e.g., three orthogonal coils) that are configured to generate electrical signals in response to the presence of an alternating electromagnetic field generated by field generators (20). Other components and techniques that may be used to generate real-time position data associated with end effector (200) may include wireless triangulation, acoustic tracking, optical tracking, inertial tracking, and the like. Some variations of ablation catheter assembly (100) may lack a position sensor.

In some versions, electrodes (250) are configured to provide both RF ablation functionality and EP mapping functionality. In some other versions, electrodes (250) are configured to provide only RF ablation functionality without also providing EP mapping functionality. In still other versions, electrodes (250) are only configured to provide EP mapping functionality without also providing RF ablation functionality. As yet another merely illustrative example, ablation catheter (120) may include some electrodes (250) that are dedicated to providing only RF ablation functionality and other electrodes that are dedicated to providing only EP mapping functionality. Other suitable configurations and functionalities that may be associated with electrodes (250) will be apparent to those skilled in the art in view of the teachings herein.

As a merely illustrative example of ablation catheter (120) that includes some electrodes (250) that are dedicated to providing only RF ablation functionality and other electrodes that are dedicated to providing only EP mapping functionality, a distal region of end effector (200) may include the electrodes that are dedicated to EP mapping. Such EP mapping electrodes may be positioned distal to electrodes (250). For instance, such EP mapping electrodes may be provided on distal hub (220), somewhere else on end effector (200) distal to flex circuit assemblies (240) (e.g., on one or more separate flex circuits), somewhere on distal regions of flex circuit assemblies (240), or elsewhere. Such EP mapping electrodes may be isolated relative to electrodes (250). Such EP mapping electrodes may be used to assist in identifying target regions for RF ablation, before the RF ablation is applied. Such EP mapping electrodes may also be used to verify whether RF ablation was sufficient, after the RF ablation is applied. Moreover, such EP mapping electrodes may monitor electrocardiogram signals in real time, during the RF ablation, to provide real-time feedback on the effectiveness of the RF ablation. In versions where EP mapping electrodes are integrated into end effector (200), lasso catheter (170) may be omitted.

III. Exemplary Alternative End Effector Configurations

Figure 9:
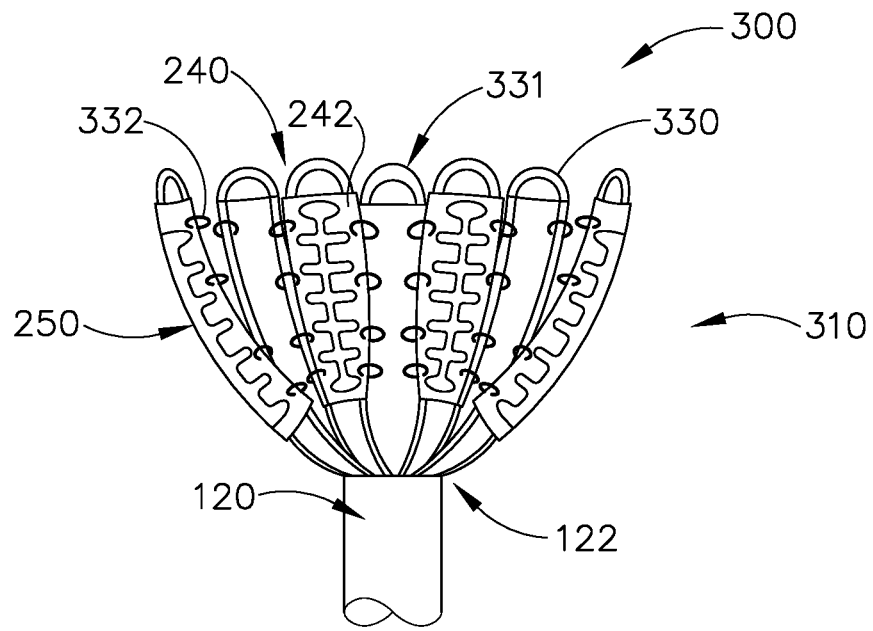
FIG. 9 depicts a side elevational view of an exemplary alternative end effector that may be incorporated into the ablation catheter assembly of FIG. 1, with an expandable assembly of the end effector in an expanded state.

FIG. 9 shows an exemplary alternative end effector (300) that may be positioned at distal end (122) of ablation catheter (120). End effector (300) of this example includes an expandable assembly (310) that is configured to transition between a non-expanded configuration and an expanded configuration, with the expanded configuration being shown in FIG. 9. In the non-expanded configuration, expandable assembly (310) may generally resemble expandable assembly (210) shown in FIG. 2A. Expandable assembly (310) may be transitioned between the expanded and non-expanded configurations in a manner like any of those described above with respect to expandable assembly (210). By way of further example only, expandable assembly (310) may be transitioned between the expanded and non-expanded configurations in accordance with any of the teachings of U.S. Pub. No. 2017/0156840, entitled "Medical Device for Modification of Left Atrial Appendage and Related Systems and Methods," published Jun. 8, 2017. Other suitable ways in which expandable assembly (310) may be transitioned between the expanded and non-expanded configurations will be apparent to those skilled in the art in view of the teachings herein.

Expandable assembly (310) of this example includes an angularly spaced array of struts (330). Struts (330) may be formed of nitinol or any other suitable material(s). Each strut (330) of this example includes a distal bend (331), such that both ends of each strut (330) are located at distal end (122) of end ablation catheter (120). In some variations, a hub (not shown) is centrally positioned between distal bends (331); and a plurality of spokes (not shown) radiate outwardly from the hub to pivotally couple the hub with distal bends (331). The spokes and hub may thus cooperate with struts (330) to transition expandable assembly (310) between the expanded and non-expanded configurations in response to relative longitudinal translation of the hub and struts (330).

Flex circuit assemblies (240) are secured to struts (330). In particular, one lateral side of each flexible substrate (242) is secured to one segment of a corresponding strut (330) on one lateral side of the distal bend (331) of that strut (330), while the other lateral side of that flexible substrate (242) is secured to the other segment of the same strut (330) on the other lateral side of the distal bend (331) of that strut (330). In the present example, flex circuit assemblies (240) are secured to struts (330) via suture loops (332), though any other suitable components and techniques as described herein may be used to secure flex circuit assemblies (240) to struts (330).

In the expanded configuration, end effector (300) of the example shown in FIG. 9 is generally shaped like a tulip or cone, rather than being bulbous like end effector (200). Alternatively, end effector (300) may have any other suitable shape when in the expanded configuration, including but not limited to hourglass-shaped, etc. End effector (300) may be used just like end effector (200) described above, with struts (330) urging electrodes (250) into contact with tissue; and with electrodes (250) being activated to provide RF ablation of the adjacent tissue. End effector (300) may also allow the flow of the patient's blood therethrough, thereby enabling the blood to serve as an irrigation fluid providing a cooling effect to avoid undue thermal damage to the tissue.

Figure 10:
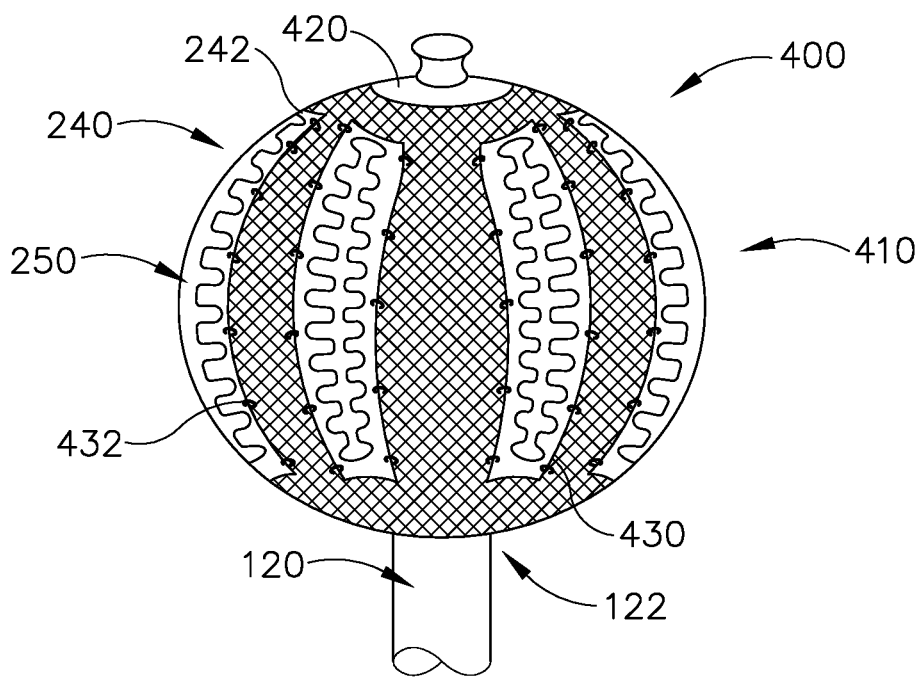
FIG. 10 depicts a side elevational view of another exemplary alternative end effector that may be incorporated into the ablation catheter assembly of FIG. 1, with an expandable assembly of the end effector in an expanded state.

FIG. 10 shows another exemplary alternative end effector (400) that may be positioned at distal end (122) of ablation catheter (120). End effector (400) of this example includes an expandable assembly (410) that is configured to transition between a non-expanded configuration and an expanded configuration, with the expanded configuration being shown in FIG. 10. In the non-expanded configuration, expandable assembly (410) may generally resemble expandable assembly (210) shown in FIG. 2A.

Expandable assembly (410) of this example includes a wire mesh or cage (430). Cage (430) may be formed of nitinol or any other suitable material(s). A distal hub (420) is secured to a distal end of cage (430). A central shaft (not shown) may pass through the center of cage (430) and be secured to distal hub (420). Expandable assembly (410) may be transitioned between the expanded and non-expanded configurations in a manner like any of those described above with respect to expandable assembly (210). Expandable assembly (410) may thus be resiliently biased to assume the expanded configuration; and a sheath (e.g., like sheath (150)) may be used to hold expandable assembly (410) in the non-expanded configuration. Alternatively, an actuator assembly may provide relative longitudinal movement between distal hub (420) and distal end (122) of ablation catheter (120) to cause cage (430) to buckle and thereby deform to the expanded configuration. Other suitable ways in which expandable assembly (410) may transition between the expanded and non-expanded configurations will be apparent to those skilled in the art in view of the teachings herein.

Flex circuit assemblies (240) are secured to cage (430). In particular, suture loops (432) are passed through openings in flex circuit assemblies and openings defined by cage (430). Alternatively, any other suitable components and techniques may be used to secure flex circuit assemblies (240) to cage (430).

In the expanded configuration, end effector (400) of the example shown in FIG. 10 is generally bulbous in shape. Alternatively, end effector (400) may have any other suitable shape when in the expanded configuration, including but not limited to conical, hourglass-shaped, etc. End effector (400) may be used just like end effector (200) described above, with cage (430) urging electrodes (250) into contact with tissue; and with electrodes (250) being activated to provide RF ablation of the adjacent tissue. End effector (400) may also allow the flow of the patient's blood therethrough, thereby enabling the blood to serve as an irrigation fluid providing a cooling effect to avoid undue thermal damage to the tissue.

Figure 11:
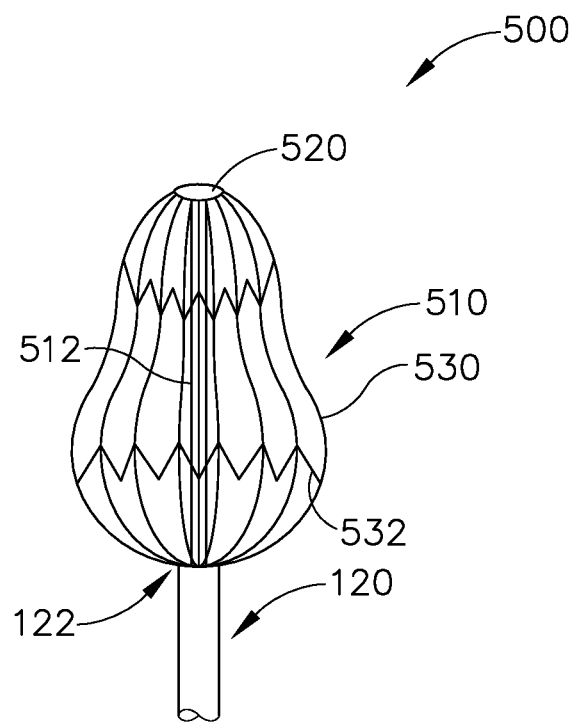
FIG. 11 depicts a side elevational view of another exemplary alternative end effector that may be incorporated into the ablation catheter assembly of FIG. 1, with an expandable assembly of the end effector in an expanded state, and with a flex circuit sleeve omitted for clarity.
Figure 12:
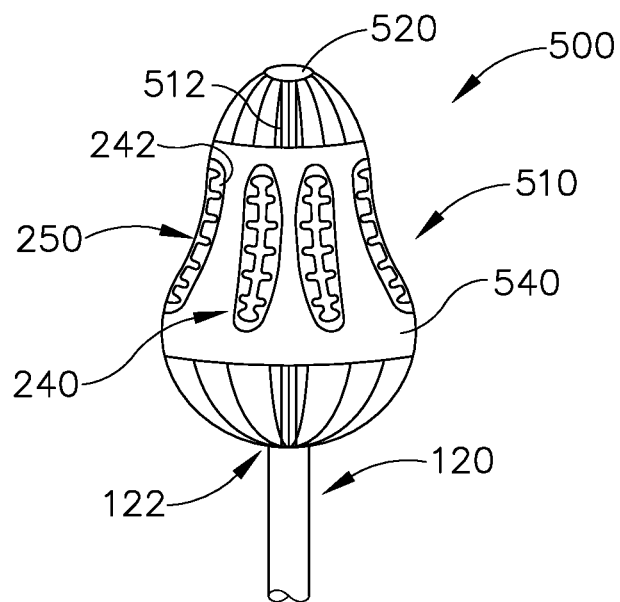
FIG. 12 depicts a side elevational view of the end effector of FIG. 11, with the expandable assembly in the expanded state, and with the flex circuit sleeve included.

FIGS. 11-12 show yet another exemplary alternative end effector (500) that may be positioned at distal end (122) of ablation catheter (120). End effector (500) of this example includes an expandable assembly (510) that is configured to transition between a non-expanded configuration and an expanded configuration, with the expanded configuration being shown in FIGS. 11-12. In the non-expanded configuration, expandable assembly (510) may generally resemble expandable assembly (210) shown in FIG. 2A.

Expandable assembly (510) of this example includes a plurality of struts (530, 532). A first set of struts (530) extend longitudinally and are positioned in an angularly spaced array. A second set of struts (532) extend between struts (530) along a generally circumferential path. In the present example, struts (532) are arranged in a distal subset and in a proximal subset. Alternatively, any other suitable number and arrangement of subsets of struts (532) may be provided. Each strut (532) has a V shape and is resiliently biased toward a generally straight configuration, such that struts (532) cooperate with each other to ensure consistent angular spacing between struts (530), preventing struts (530) from bunching together and helping struts (530) to keep their shape. In some variations, struts (532) are omitted.

A distal hub (520) is secured to a distal end of struts (530). A central shaft (512) passes through the center of expandable assembly (510) and is secured to distal hub (520). Expandable assembly (510) may be transitioned between the expanded and non-expanded configurations in a manner like any of those described above with respect to expandable assembly (210). Expandable assembly (510) may thus be resiliently biased to assume the expanded configuration, and a sheath (e.g., like sheath (150)) may be used to hold expandable assembly (510) in the non-expanded configuration. Alternatively, an actuator assembly may provide relative longitudinal movement between distal hub (520) and distal end (122) of ablation catheter (120) to cause struts (530) to buckle and thereby deform to the expanded configuration. Other suitable ways in which expandable assembly (510) may transition between the expanded and non-expanded configurations will be apparent to those skilled in the art in view of the teachings herein.

Flex circuit assemblies (240) are secured to a sleeve (540). Sleeve (540) may be formed of any suitable material(s), including but not limited to polymers such as nylon, polyester (e.g., Dacron), polypropylene, ePTFE, polyurethane, etc. Some variations of sleeve (540) may include one or more slits or openings formed therethrough, to facilitate communication of fluids therethrough. By way of example only, flex circuit assemblies (240) may be secured to sleeve (540) via heat fusion, stitching, suture loops, rivets, or using any other suitable components or techniques. In some variations, the wire (262) of each flex circuit assembly (242) is woven into sleeve (540). Sleeve (540) of the present example is fitted over struts (530, 532) to thereby secure flex circuit assemblies (240) relative to struts (530, 532). By way of example only, sleeve (540) may be secured to struts (530) via stitching, suture loops, rivets, or using any other suitable components or techniques. In some versions, sleeve (540) promotes consistent angular spacing between struts (530), prevents struts (530) from bunching together, and helps struts (530) to keep their shape. Sleeve (540) may also reduce the risk of tissue getting captured and pinched between struts (530).

In the expanded configuration, end effector (500) of the example shown in FIGS. 11-12 is generally pear-shaped, with the distal region of end effector (500) being narrower than the proximal region of end effector (500). In some other variations, end effector (500) is still pear-shaped in the expanded configuration, yet the distal region of end effector (500) is wider than the proximal region of end effector (500). Alternatively, end effector (500) may have any other suitable shape when in the expanded configuration, including but not limited to conical, hourglass-shaped, etc. End effector (500) may be used just like end effector (200) described above, with expandable assembly (510) urging electrodes (250) into contact with tissue; and with electrodes (250) being activated to provide RF ablation of the adjacent tissue. End effector (500) may also allow the flow of the patient's blood therethrough, thereby enabling the blood to serve as an irrigation fluid providing a cooling effect to avoid undue thermal damage to the tissue.

While sleeve (540) is only shown in the context of end effector (500), any of the other end effectors (200, 300, 400) described herein may be readily modified to incorporate a sleeve (540). In other words, flex circuit assemblies (240) may be secured to any of the expandable assemblies (210, 310, 410, 510) described herein via a sleeve (540) or variations thereof.

Just as end effector (200) may have variations that include EP mapping electrodes in addition to including RF ablation electrodes (250), end effectors (300, 400, 500) may also have EP mapping electrodes in addition to having electrodes (250). As with end effector (200), such EP mapping electrodes may be positioned distal to electrodes (250) and may be electrically isolated relative to electrodes (250).

In various examples described above, flex circuit assemblies (240) may be secured to expandable assemblies (210, 310, 410, 510) without the use of adhesives. In other words, flex circuit assemblies (240) may be secured to expandable assemblies (210, 310, 410, 510) via suture loops (232, 332, 432), rivets (290), stitched suture (282), sleeve (540), or some other mechanical/non-adhesive structure. In the process of assembling end effectors (200, 300, 400, 500), robotic systems may be readily implemented to apply suture loops (232, 332, 432), to form rivet (290), to stitch suture (282), or to provide any other form of securing of flex circuit assemblies (240) to expandable assemblies (210, 310, 410, 510) as contemplated herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a catheter, wherein at least a portion of the catheter is sized and configured to fit within a lumen of a human cardiovascular system; and (b) an end effector positioned at a distal end of the catheter, wherein the end effector comprises: (i) an expandable assembly, wherein the expandable assembly is configured to transition between a non-expanded state and an expanded state, wherein the expandable assembly comprises at least one deformable strut or cage, and (ii) at least one flex circuit, wherein each flex circuit of the at least one flex circuit comprises: (A) a flexible substrate secured to the expandable assembly without adhesive, and (B) an electrode secured to the flexible substrate, wherein the expandable assembly in the expanded state is configured to urge the electrode into contact with tissue, the electrode having a fishbone-like configuration that defines a longitudinally elongated portion and a plurality of fingers extending transversely from the longitudinally elongated portion.

Example 2

The apparatus of Example 1, wherein the expandable assembly comprises a plurality of longitudinally extending struts angularly spaced apart from each other in an array about a longitudinal axis.

Example 3

The apparatus of Example 2, wherein the struts are configured to transition between a generally straight configuration and an outwardly bowed configuration to thereby transition the expandable assembly between the non-expanded state and the expanded state, respectively.

Example 4

The apparatus of any one or more of Examples 2 through 3, wherein the flexible substrate of each flex circuit is secured to a corresponding pair of struts of the plurality of struts, wherein each strut of the plurality of struts comprises a self-expanding member.

Example 5

The apparatus of Example 4, wherein each strut comprises at least one coupling tab, wherein the flexible substrate of each flex circuit is secured to the at least one coupling tab of each strut of the corresponding pair of struts.

Example 6

The apparatus of any one or more of Examples 2 through 5, the end effector further comprising a distal hub, wherein distal portions of the struts are secured to the distal hub.

Example 7

The apparatus of Example 6, further comprising a central shaft secured to the hub, wherein the shaft extends through the expandable assembly, wherein the expandable assembly is configured to transition between the non-expanded state and the expanded state in response to relative longitudinal movement between the distal end of the catheter and the combination of the hub and the central shaft.

Example 8

The apparatus of any one or more of Examples 2 through 5, wherein each strut includes a pair of longitudinally extending segments and a distal bend joining the longitudinally extending segments.

Example 9

The apparatus of any one or more of Examples 2 through 8, wherein the expandable assembly further comprises a plurality of circumferentially extending struts extending between the longitudinally extending struts.

Example 10

The apparatus of Example 9, wherein the circumferentially extending struts are configured to urge the longitudinally extending struts angularly away from each other.

Example 11

The apparatus of any one or more of Examples 1 through 10, wherein the end effector further comprises a sleeve positioned over the expandable assembly, wherein the at least one flex circuit is secured to the sleeve.

Example 12

The apparatus of Example 11, wherein the sleeve comprises a textile material.

Example 13

The apparatus of any one or more of Examples 1 through 12, wherein the at least one flex circuit is secured to the expandable assembly via one or more sutures.

Example 14

The apparatus of any one or more of Examples 1 through 12, wherein the at least one flex circuit is secured to the expandable assembly via one or more rivets.

Example 15

The apparatus of Example 14, wherein the one or more rivets are formed of a monofilament polymer.

Example 16

The apparatus of any one or more of Examples 1 through 15, wherein the expandable assembly is configured to form a bulbous shape in the expanded state.

Example 17

The apparatus of any one or more of Examples 1 through 15, wherein the expandable assembly is configured to form a conical shape in the expanded state.

Example 18

The apparatus of any one or more of Examples 1 through 15, wherein the expandable assembly is configured to form a pear shape in the expanded state.

Example 19

An apparatus comprising: (a) a catheter, wherein at least a portion of the catheter is sized and configured to fit within a lumen of a human cardiovascular system; and (b) an end effector positioned at a distal end of the catheter, wherein the end effector comprises: (i) an expandable wire frame assembly, wherein the expandable wire frame assembly is configured to transition between a non-expanded state and an expanded state, and (ii) at least one flex circuit, wherein each flex circuit of the at least one flex circuit comprises: (A) a flexible substrate secured to the expandable wire frame assembly via one or more structures selected from the group consisting of loops, rivets, or stitches, and (B) an electrode secured to the flexible substrate, wherein the expandable wire frame assembly in the expanded state is configured to urge the electrode into contact with tissue.

Example 20

An electrophysiology device comprising: (a) an expandable assembly, wherein the expandable assembly is configured to mechanically transition between a non-expanded state and an expanded state; (b) a sleeve positioned about the expandable assembly; and (c) at least one flex circuit, wherein each flex circuit of the at least one flex circuit comprises: (i) a flexible substrate secured, without adhesive, to the sleeve, and (ii) an electrode secured to the flexible substrate, the electrode having a fishbone-like configuration that defines a longitudinally elongated portion and a plurality of fingers extending transversely from the longitudinally elongated portion, wherein the expandable assembly in the expanded state is configured to urge the electrode into contact with tissue.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a catheter, wherein at least a portion of the catheter is sized and configured to fit within a lumen of a human cardiovascular system; and
   (b) an end effector positioned at a distal end of the catheter, wherein the end effector comprises:
      (i) an expandable assembly, wherein the expandable assembly is configured to transition between a non-expanded state and an expanded state, wherein the expandable assembly comprises a plurality of longitudinally extending deformable struts extending from a proximal end of the end effector toward a distal end of the end effector, and
      (ii) at least one flex circuit, wherein each flex circuit of the at least one flex circuit comprises:
         (A) a flexible substrate secured to and laterally between a corresponding pair of the deformable struts without adhesive, and
         (B) an electrode secured to the flexible substrate, wherein the expandable assembly in the expanded state is configured to urge the electrode into contact with tissue, the electrode having a fishbone-like configuration that defines a longitudinally elongated portion and a plurality of fingers extending transversely from the longitudinally elongated portion.

2. The apparatus of claim 1, wherein the struts are angularly spaced apart from each other in an array about a longitudinal axis.

3. The apparatus of claim 2, wherein the struts are configured to transition between a generally straight configuration and an outwardly bowed configuration to thereby transition the expandable assembly between the non-expanded state and the expanded state, respectively.

4. The apparatus of claim 2, wherein each strut comprises a self-expanding member.

5. The apparatus of claim 4, wherein each strut comprises at least one coupling tab, wherein the flexible substrate of each flex circuit is secured to the at least one coupling tab of each strut of the corresponding pair of struts.

6. The apparatus of claim 2, the end effector further comprising a distal hub, wherein distal portions of the struts are secured to the distal hub.

7. The apparatus of claim 6, further comprising a central shaft secured to the hub, wherein the shaft extends through the expandable assembly, wherein the expandable assembly is configured to transition between the non-expanded state and the expanded state in response to relative longitudinal movement between the distal end of the catheter and the combination of the hub and the central shaft.

8. The apparatus of claim 2, wherein each strut includes a pair of longitudinally extending segments and a distal bend joining the longitudinally extending segments.

9. The apparatus of claim 2, wherein the expandable assembly further comprises a plurality of circumferentially extending struts extending between the longitudinally extending struts.

10. The apparatus of claim 9, wherein the circumferentially extending struts are configured to urge the longitudinally extending struts angularly away from each other.

11. The apparatus of claim 2, wherein the end effector further comprises a sleeve positioned over the expandable assembly, wherein the at least one flex circuit is secured to the sleeve.

12. The apparatus of claim 11, wherein the sleeve comprises a textile material.

13. The apparatus of claim 1, wherein the at least one flex circuit is secured to the expandable assembly via one or more sutures.

14. The apparatus of claim 1, wherein the at least one flex circuit is secured to the expandable assembly via one or more rivets.

15. The apparatus of claim 14, wherein the one or more rivets are formed of a monofilament polymer.

16. The apparatus of claim 1, wherein the expandable assembly is configured to form a bulbous shape in the expanded state.

17. The apparatus of claim 1, wherein the expandable assembly is configured to form a conical shape in the expanded state.

18. The apparatus of claim 1, wherein the expandable assembly is configured to form a pear shape in the expanded state.

19. An apparatus comprising:
   (a) a catheter, wherein at least a portion of the catheter is sized and configured to fit within a lumen of a human cardiovascular system; and
   (b) an end effector positioned at a distal end of the catheter, wherein the end effector comprises:
      (i) an expandable wire frame assembly formed by a plurality of struts angularly spaced apart from each other, wherein the expandable wire frame assembly is configured to transition between a non-expanded state and an expanded state, and
      (ii) a plurality of flex circuits, wherein each flex circuit of the plurality of flex circuits comprises:
         (A) a flexible substrate secured to the expandable wire frame assembly via one or more structures selected from the group consisting of loops, rivets, or stitches, the flexible substrate being outwardly positioned in relation to the expandable wire frame assembly, the flexible substrate including an outwardly facing surface, and (B) an electrode secured to the outwardly facing surface of the flexible substrate, wherein the expandable wire frame assembly in the expanded state is configured to urge the electrode into contact with tissue, each flexible substrate being secured to a corresponding pair of struts of the plurality of struts such that the flexible substrates are angularly spaced apart from each other by the plurality of struts.

20. An apparatus comprising:
(a) a catheter, wherein at least a portion of the catheter is sized and configured to fit within a lumen of a human cardiovascular system; and (b) an end effector positioned at a distal end of the catheter, wherein the end effector comprises:

an expandable assembly, wherein the expandable assembly is configured to transition between a non-expanded state and an expanded state, wherein the expandable assembly comprises a plurality of longitudinally extending deformable struts extending from a proximal end of the end effector toward a distal end of the end effector, and (ii) at least one flex circuit, wherein each flex circuit of the at least one flex circuit comprises:

(A) a flexible substrate secured to and laterally between a corresponding pair of the deformable struts, and (B) an electrode secured to the flexible substrate, wherein the expandable assembly in the expanded state is configured to urge the electrode into contact with tissue.

* * * * *

UNITED STATES PATENT AND TRADEMARK OFFICE
CERTIFICATE OF CORRECTION

PATENT NO. : 11,642,165 B2
APPLICATION NO. : 16/023644
DATED : May 9, 2023
INVENTOR(S) : Patrick J. Kiernan et al.

It is certified that error appears in the above-identified patent and that said Letters Patent is hereby corrected as shown below:

In the Claims
Column 20, Line 3, Claim 20   Before "an"
Insert -- (i) --

Signed and Sealed this
Twenty-fifth Day of July, 2023

Katherine Kelly Vidal
*Director of the United States Patent and Trademark Office*